United States Patent [19]

Powles et al.

[11] Patent Number: 5,653,694

[45] Date of Patent: Aug. 5, 1997

[54] ASPIRATION NEEDLE APPARATUS INCORPORATING ITS OWN VACUUM AND METHOD AND ADAPTER FOR USE THEREWITH

[75] Inventors: Trevor J. Powles, Surrey, United Kingdom; Mir A. Imran, Palo Alto, Calif.

[73] Assignee: Advanced Cytometrix, Inc., Sunnyvale, Calif.

[21] Appl. No.: 504,928

[22] Filed: Jul. 20, 1995

Related U.S. Application Data

[63] Continuation-in-part of Ser. No. 421,064, Apr. 13, 1995, abandoned.

[51] Int. Cl.[6] ............................. A61M 5/00; A61M 5/31
[52] U.S. Cl. ........................ 604/240; 604/411; 128/763
[58] Field of Search ........................... 604/240, 207, 604/206, 403, 411, 410, 412, 413, 414, 415, 900, 200, 212, 216, 217, 185, 272, 82, 86, 87, 88, 35, 36, 190, 134, 136, 273, 274; 128/752, 763, 764, 765, 770

[56] References Cited

U.S. PATENT DOCUMENTS

| | | | |
|---|---|---|---|
| 3,484,849 | 12/1969 | Huebner et al. | 604/413 X |
| 3,724,460 | 4/1973 | Gomez et al. | 604/88 |
| 3,797,488 | 3/1974 | Hurschman et al. | 604/136 |
| 3,967,621 | 7/1976 | Schwarz | 604/206 X |
| 4,935,020 | 6/1990 | Broden | 604/411 |
| 5,017,191 | 5/1991 | Yamada et al. | 604/243 |
| 5,030,207 | 7/1991 | Mersch et al. | 604/168 |
| 5,128,048 | 7/1992 | Stewart et al. | 210/749 |
| 5,181,523 | 1/1993 | Wendelborn | 128/764 |
| 5,251,786 | 10/1993 | Sarrine | 604/205 X |
| 5,358,501 | 10/1994 | Meyer | 604/414 |
| 5,400,923 | 3/1995 | Golias et al. | 222/82 |
| 5,496,301 | 3/1996 | Hlavinka et al. | 604/409 |
| 5,511,558 | 4/1996 | Shepard et al. | 128/760 |

*Primary Examiner*—Michael Buiz
*Assistant Examiner*—V. Alexander
*Attorney, Agent, or Firm*—Flehr Hohbach Test Albritton & Herbert LLP

[57] ABSTRACT

An aspiration needle apparatus for collecting cell samples from tissue by the use of a vacuum container having an enclosed evacuated space sealed by a penetrable diaphragm. An adapter has a recess to receive the vacuum container. A needle is carried by the adapter and serves as an aspiration needle to collect a cell sample and penetrates the diaphragm to couple the evacuated space to the flow passage of the needle means.

20 Claims, 5 Drawing Sheets

ASPIRATION NEEDLE APPARATUS INCORPORATING ITS OWN VACUUM AND METHOD AND ADAPTER FOR USE THEREWITH

CROSS-REFERENCE TO RELATED APPLICATION

This application is a continuation-in-part of application Ser. No. 08/421,064 filed on Apr. 13, 1995, now abandoned.

FIELD OF THE INVENTION

This invention relates to an aspiration needle apparatus incorporating its own vacuum and a method and adapter for use therewith. In fine needle aspiration technology, there has been a need for applying a vacuum to the needle to accomplish the aspiration. Typically this has been accomplished by use of a syringe and in certain occasions by the application of a vacuum to the needle by a vacuum pump under the control of the physician performing the aspiration procedure. There is a need for a simplified apparatus for accomplishing fine needle aspiration.

SUMMARY OF THE INVENTION

In general, it is an object of the present invention to provide an aspiration needle apparatus incorporating its own vacuum and a method and adapter for use therewith.

Another object of the invention is to provide a removable adapter which can be utilized for mating an aspiration needle to a vacuum container.

Another object of the invention is to provide an apparatus and method and adapter for use therewith which makes it possible to readily establish a vacuum condition in the needle apparatus and to thereafter break the vacuum.

Another object of the invention is to provide an adapter of the above character which can be used repeatedly.

Another object of the invention is to provide an aspiration needle apparatus of the above character in which first and second needles are provided for first communicating with the vacuum and thereafter for breaking the vacuum.

Another object of the invention is to provide an aspiration needle apparatus of the above character in which only a single needle is required.

Another object of the invention is to provide an aspiration needle apparatus and method of the above character in which the specimen cell sample can be sucked out of the needle through a second vacuum container along with a medium.

Another object of the invention is to provide an aspiration needle apparatus and method of the above character in which the cell sample along with the medium can be shipped in the second vacuum container to a laboratory for analysis.

Additional objects and features of the invention will appear form the following description in which the preferred embodiments are set forth in detail in conjunction with the company drawings.

DESCRIPTION OF THE PREFERRED EMBODIMENT

In general, the aspiration needle apparatus of the present invention is used for collecting cell samples from tissue by the use of a vacuum container having an enclosed evacuated space sealed by a penetrable diaphragm. An adapter is provided which has a recess therein adapted to receive the vacuum container. Needle means is carried by the adapter and has a distal extremity serving as an aspiration needle for entering the tissue to collect the cell sample. The needle means also has a proximal extremity disposed in the recess of the adapter and is capable of penetrating the diaphragm of the vacuum container when it is inserted into the recess to couple the evacuated space in the vacuum container to the needle means. After the cell sample has been collected, the vacuum container can be removed and another or second vacuum container inserted into the recess with the aspiration needle being inserted into a medium and then having the proximal extremity of the needle means penetrate the diaphragm of the second vacuum container to supply a vacuum to suck out the cell sample collected by the aspiration needle and to bring therewith medium. The second vacuum container can thereafter be removed from the adapter and supplied to a laboratory for analysis.

Figures 1, 2, 3:
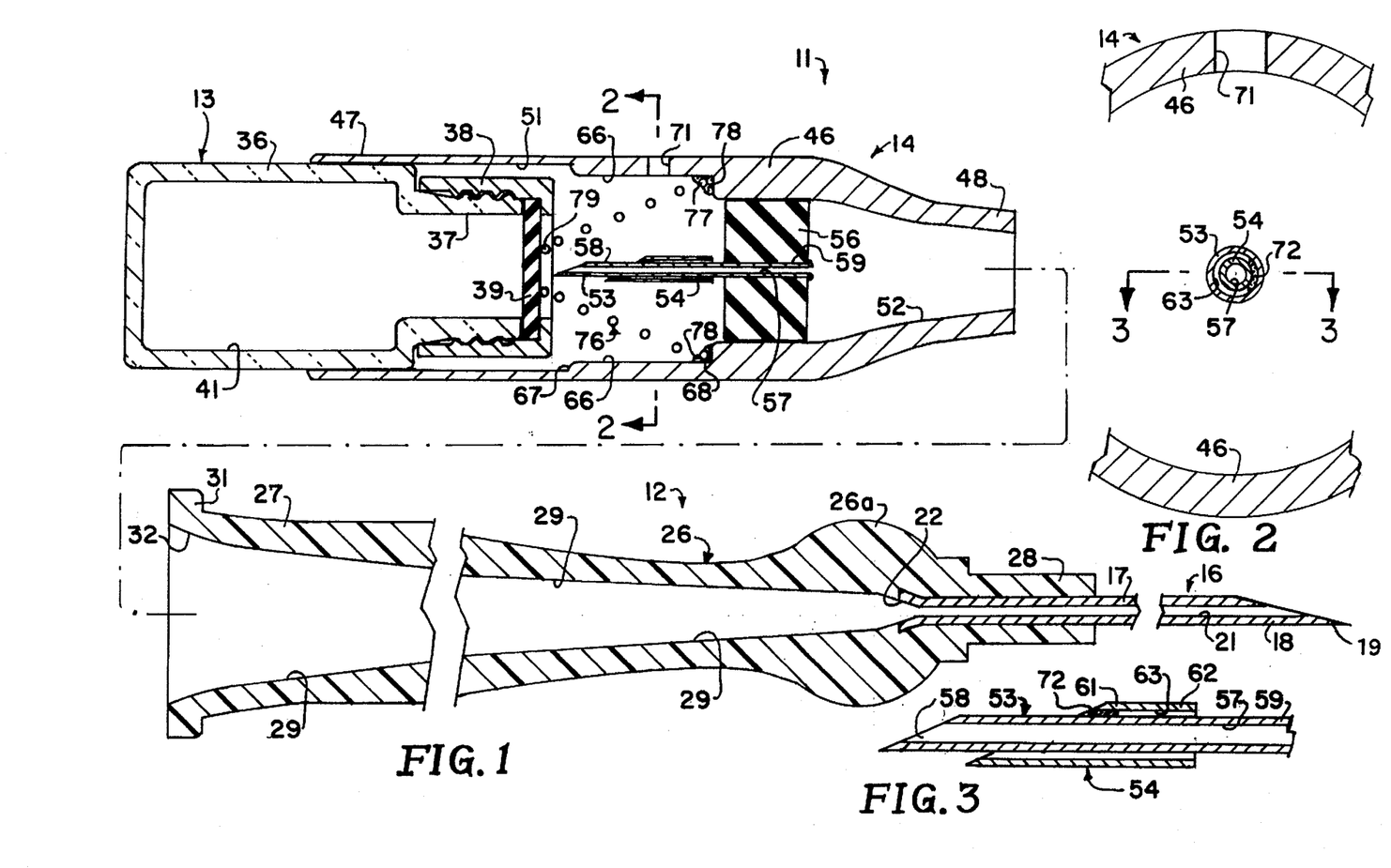
FIG. 1 is a side elevational view in section of an aspiration needle apparatus incorporating its own vacuum which includes the aspiration needle, an adapter and a vacuum container.
FIG. 2 is an enlarged cross-sectional view taken along the line 2—2 of FIG. 1.
FIG. 3, is a cross-sectional view taken along the line 3—3 of FIG. 2.

More in particular as shown in FIGS. 1–3 of the drawings, the aspiration needle apparatus 11 incorporating its own vacuum consists of an aspiration needle 12, a vacuum container 13 and an adapter 14 for mating the vacuum container 13 to the aspiration needle 12.

The aspiration needle 12 is of the type described in copending application Ser. No. 08/228,551 filed Apr. 15, 1994 consisting of a rigid elongate tubular member 16 formed of a suitable material such as stainless steel having a length of 2 to 8 centimeters and of a suitable diameter as for example 23 gauge. The rigid elongate tubular member 16 is provided with proximal and distal extremities 17 and 18 in which the distal extremity is sharpened to form a needle point 19. The rigid elongate tubular member 16 is provided with a flow passage 21 extending from the distal extremity 18 to the proximal extremity 17. The proximal extremity 17 is flared outwardly to provide a funnel-shaped recess 22 leading into the flow passage 21.

A body 26 is mounted on the proximal extremity 17 of the rigid tubular member 16 and is formed of a suitable plastic as for example ULTEM. The body 26 is provided with proximal and distal extremities 27 and 28. The body 26 is provided with a conical chamber 29 extending from the proximal extremity 27 to the distal extremity 28. The body 26 is provided with a spherical enlarged portion 26a which circumscribes the conical chamber 29 in the region immediately adjacent the funnel shaped recess 22 which serves as a convex lens to magnify that portion of the container for viewing aspirate as hereinafter described. The body 26 is provided with a hub 31 on the proximal extremity 27 that has a tapered conical recess 32 which adjoins the conical chamber 29. The body 26 is provided with an annular recess 33 proximal of the enlarged portion 26a which is adapted to be engaged by fingers of the hand for controlling and movement of the needle for a purpose hereinafter described.

The vacuum container 13 is in the form of a vacuum bottle 36 formed of a suitable material such as glass. The glass bottle is of a conventional construction and is generally cylindrical in shape and is provided with a neck 37 of reduced diameter that has been threaded to receive a threaded cap 38. The cap 38 is provided with a cell-sealing diaphragm or membrane 39 formed of a suitable cell sealing elastomeric material which can be readily penetrated by a conventional surgical needle. The vacuum container 13 encloses an evacuated space 41 of a suitable size as for example 15 to 30 milliliters and preferably approximately 20 milliliters. This space 41 as shown in FIG. 1 is devoid of a solid or liquid and is devoted solely to providing the desired vacuum. The space 41 can be evacuated to a vacuum below ambient or atmospheric or a sub-ambient pressure ranging from 15 to 20" of mercury.

The adapter 14 consists generally of a cylindrical body 46 which can be formed of a suitable material such as a transparent plastic, i.e., a polycarbonate or an acrylic. The body 46 is provided with proximal and distal extremities 47 and 48. The distal extremity 48 is necked down as shown in FIG. 1 and is adapted to be removably mounted on the hub 31 of the body 26 to form a fluid-tight seal therewith. Cooperative mating means is provided on the proximal extremity 48 of the body 46 and on the vacuum container 13. Thus as shown in FIG. 1 the proximal extremity 47 is provided with a cylindrical recess 51 which is adapted to receive the vacuum container 13. A flow passage 52 is provided extending from the cylindrical recess 51 through the distal extremity 48 so that it is in communication with the conical recess 29 of the aspiration needle 12.

Needle means is carried by the adapter body 46 for establishing a connection between the flow passage 52, the interior of the vacuum container 13 first for supplying a vacuum to the flow passage 52 and thereafter to break the vacuum being supplied to the flow passage 52. Such needle means is shown in FIG. 1 and consists of first and second needles 53 and 54 formed of a suitable material such as stainless steel. As shown, the first and second needles 53 and 54 are carried by the body 46 and are disposed within the passage 52. The first needle 53 is mounted in a resilient plug or block 56 frictionally retained in the flow passage 52 of the body 46 and formed of a suitable material such as rubber through which the first needle 53 extends. The first needle is provided with a flow passage 57 which extends from a proximal sharpened tip 58 to a distal extremity 59 extending through the plug 56 and opening into the flow passage 52 in the body 46.

The second needle 54 is provided with a proximal extremity 61 and a distal extremity 62. As shown particularly in FIGS. 1 and 2, the second needle 54 is sized so that it can be coaxially mounted on the exterior of the first needle 53 and form an annular flow passage 63 extending from the proximal extremity 61 to the distal extremity 62 and opening into a chamber 66 that is defined by annular shoulders 67 and 68 and which is open to the atmosphere through a hole 71. As can be seen, the proximal extremity 61 of the second needle 54 is sharpened as shown and is distal of the proximal extremity 58 of the first needle 53 by a suitable distance as for example ½" for a purpose hereinafter described. The second needle 54 is supported on the first needle 53 in a suitable manner such as by use of an adhesive or solder 72 within the annular passage 63 as shown particularly in FIG. 2.

Yieldable means in the form of a spring 76 is provided within the chamber 66 and has a larger distal or base end 77 engaging the shoulder 68 and retained in engagement therein by suitable means such as an adhesive 78. The smaller or proximal end 79 of the spring 76 yieldably engages the diaphragm or membrane 39 so as to retain the membrane or diaphragm 39 out of engagement with the sharp end of the first needle 53.

Operation and use of the aspiration needle apparatus 11 may now be briefly described. Let it be assumed that it is desired to perform an aspiration procedure after a physician or surgeon has found a palpable breast tumor by utilizing the apparatus of the present invention for obtaining a cell sample from the breast tumor by withdrawing aspirate from the breast tumor. The apparatus 11 is assembled with the adapter 14 inserted into the conical recess 32 of the needle. The vacuum container 13 is disposed in the adapter 14 with the proximal extremity 58 of the needle 53 distal of the membrane 39 as shown in FIG. 1. The surgeon using one hand for locating the palpable breast tumor utilizes the other hand to grasp the aspiration needle apparatus 11 by two fingers as for example the thumb and forefinger to grasp the annular recess 33 of the aspiration needle 12 and pushes the needle to penetrate the skin of the breast and to enter into the breast tissue and to lodge the distal extremity of the aspiration needle 12 within the tumor. As soon as the surgeon is assured that the needle 12 is lodged into the appropriate position with the tumor.

Figure 4:
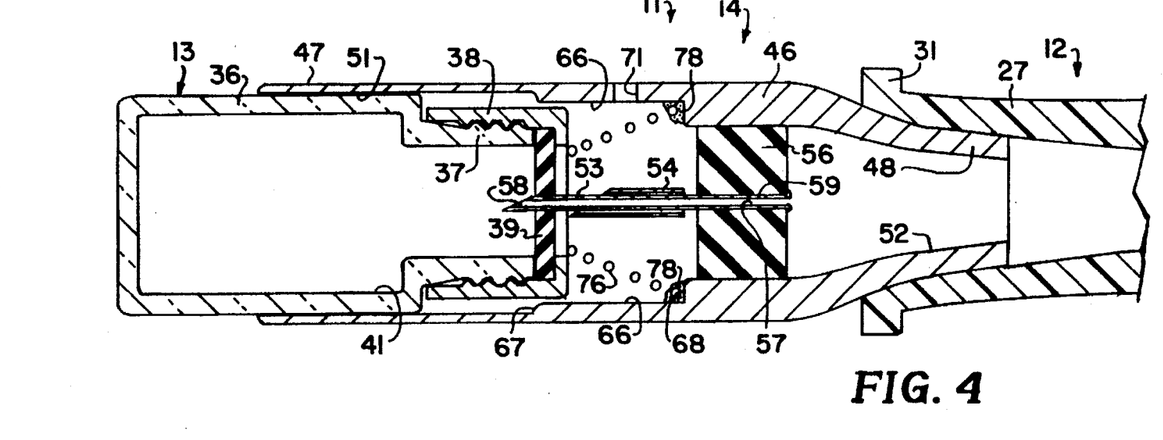
FIG. 4 is a view similar to that shown in FIG. 1 but showing the vacuum in the vacuum container being applied to the needle.

The surgeon or physician using the forefinger of the hand holding the aspiration needle apparatus 11 engages the vacuum container 13 and presses it distally against the force of the spring 76 to cause relative movement between the adapter 14 and the vacuum container 13 to a first position to cause the sharpened proximal extremity 58 of the first needle 53 to puncture the diaphragm or membrane 39 carried by the container 36 to expose the evacuated space 41 to the interior flow passage 57 of the first inner needle 53 (see FIG. 4). This in turn exposes the flow passage in the body 46 and the conical chamber 29 in the aspiration needle 12 and the flow passage 21 in the elongate tubular member 16 to create a sub-ambient condition within the tumor to cause cells of the tumor to be withdrawn from the tumor as an aspirate into the flow passage 21 and to bring the aspirate into the chamber 29 where the entrance of the aspirate into the chamber can be observed visually through the magnifying lens framed by the spherical portion 26a as shown in FIG. 3.

Figure 5:
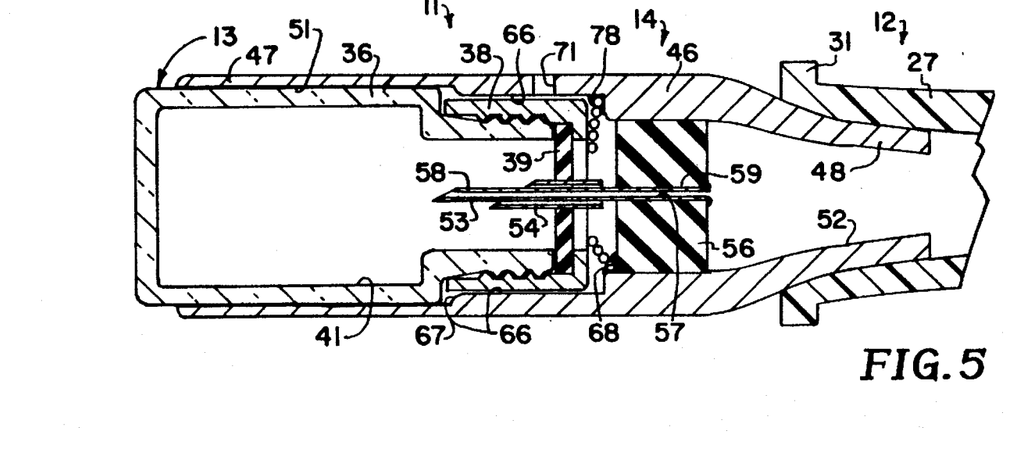
FIG. 5 is a view similar to FIG. 4 but showing the vacuum to the needle being broken.

As soon as it has been ascertained that sufficient aspirate has been drawn into the chamber 29, the subambient pressure being applied to the rigid elongate tubular member can be terminated or broken by the physician pushing the vacuum container 13 in the form of a vacuum bottle 36 an additional distance proximally against the force of the yieldable spring 76 to a second position so that the second needle 54 has its proximal extremity 61 penetrating through the diaphragm 39 as shown in FIG. 5. As soon as the proximal extremity 61 penetrates into the space, 41, atmospheric air can enter into the space passing through the hole 71 in the body 46 and into the annular flow passage 63 in the second needle 54 and into the space 41. Thus it can be seen as soon as the second needle 54 punctures the diaphragm 39 the subambient pressure applied to the aspiration needle 12 will be abruptly terminated so that no further aspirate is withdrawn from the tumor.

When the cell sample has been collected in the aspirate within the chamber 29, the aspirate remains within the chamber 29. As soon as the desired cell sample has been collected, the aspiration needle 12 can be withdrawn from the tumor with the adapter 14 and the vacuum container in place. Alternatively if desired, the adapter 14 containing the vacuum container 13 can be removed before withdrawing the aspiration needle 12.

Figure 6:
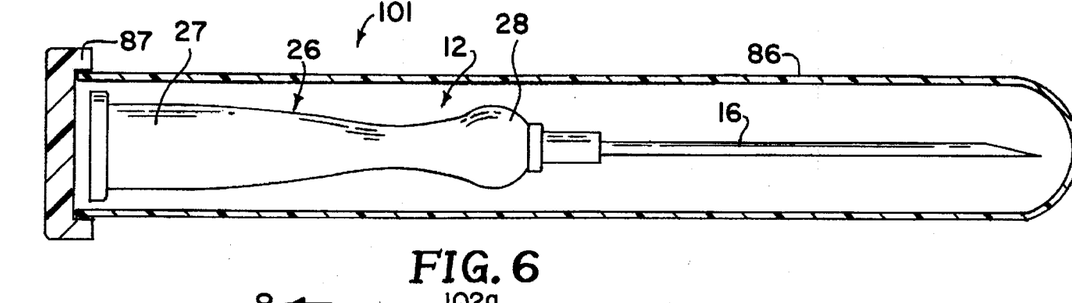
FIG. 6 is a side-elevational view in section showing an aspiration needle with a collected cell sample in a sealed container for transportation to a laboratory.

Thereafter, the aspiration needle 12 can be handled in the manner hereinbefore described in connection with the copending application Ser. No. 08/228,551 filed Apr. 15, 1994. As described therein, the aspirate can be discharged onto slides which are shipped to laboratory for analysis or alternatively, the entire needle with the cell sample with the aspirate therein can be supplied to the laboratory for analysis. Thus, as shown in FIG. 6, the aspiration needle 12 with the collected cell sample therein can be placed in a test tube-like container 86 formed of a suitable material such as plastic and sealed with a removable cap 87 for transportation to a laboratory for analysis.

Figures 7, 8:
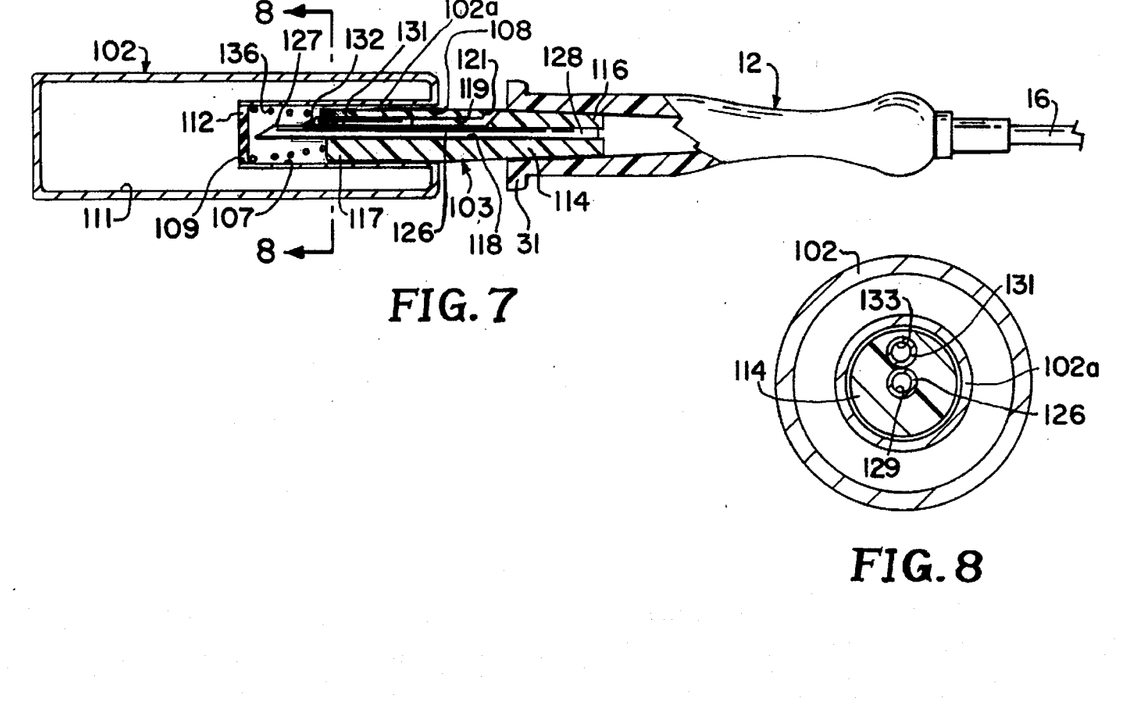
FIG. 7 is a side elevational view of another embodiment of the present invention.
FIG. 8 is a cross sectional view taken along the lines 8—8 of FIG. 5.

Another embodiment of an aspiration needle apparatus incorporating the present invention is shown in FIGS. 5 and 8. As shown therein, the needle aspiration apparatus 101 consists of aspiration needle 12 identical to that hereinbefore described and a vacuum container 102 and an adapter 103. As shown, the vacuum container 102 can be in the form of a metal canister or container that is in the form of an elongate cylinder and having an internal cylindrical portion 102a disposed coaxially therein. The cylindrical portion 102a defines a cylindrical chamber or recess 107 extending axially of the cylindrical portion 102a which opens through an opening 108 open to the atmosphere provided in one end of the metal container 102. The other end of the cylindrical recess 107 is open through an opening 109 into an interior evacuated annular space 111 in the vacuum container 102 through a cell-sealing diaphragm or membrane 112 mounted therein by suitable means such as an adhesive (not shown) to close off that end of the cylindrical recess 107. The cylindrical recess 107 is sized so it can serve as a female adapter for receiving the cylindrical male adapter 103 in the form of a cylindrical body 114 formed of a suitable material such as a transparent plastic of the type hereinbefore described and is provided with the proximal and distal extremities 116 and 117. It is provided with a flow passage 118 extending from the proximal extremity 116 to the distal extremity 117. It is also provided with an additional flow passage 119 that is generally parallel to the passage 118 and extends from the proximal extremity to a point intermediate the proximal and distal extremities 116 and 117 and is in communication with a sidewise extending port 121 that is positioned so it is always open to the atmosphere for a purpose hereinafter described.

A first needle 126 formed of a suitable material such as stainless steel which has a sharpened tapered proximal extremity 127 and a distal extremity 128 is disposed within the flow passage 118 and is retained therein in a suitable manner such as by an adhesive (not shown). The first needle 126 is provided with a flow passage 129 that extends from the proximal extremity 127 to the distal extremity 128 of the needle and opens into the flow passage 118. Similarly, a second needle 131 having a sharpened proximal extremity 132 and a distal extremity 134 is mounted within the body 114 by suitable means such as an adhesive (not shown). It has a flow passage 133 extending from the sharpened proximal extremity 132 to the distal extremity 134 which is in communication with the flow passage 119 that opens to the atmosphere through the port 121 as hereinbefore described. As shown in FIG. 7, the proximal extremities 116 and 127 of the first and second needles 126 and 131 are staggered so that the first needle 126 extends proximally for a suitable distance as for example approximately ¼ to ½" beyond the proximal extremity 127 so that the first and second needles 126 and 131 can sequentially penetrate the diaphragm 112 as hereinafter described. The proximal extremity of the body 116 is tapered as shown so that it can make a tight friction fit with the hub 31 of the aspiration needle 12 to provide a fluid-tight seal therebetween.

A conical coil spring 136 is disposed within the cylindrical recess 107 and is secured therein by suitable means such as an adhesive (not shown) and extends distally from the diaphragm 112 and is adapted to be engaged by the adapter 103 when it is inserted into the cylindrical recess 107. The coil spring 136 serves to prevent inadvertent puncturing of the diaphragm 112 by the first and second needles 126 and 131.

Operation and use of the aspiration needle apparatus 101 as shown in FIGS. 7 and 8 is very similar to that shown in FIG. 1 with the exception that the vacuum container 13 shown in FIG. 1 is in the form of a male member adapted to mate with an adapter 14 which is constructed as a female member providing a chamber 66 for receiving the vacuum container 13. Conversely, with the embodiment shown in FIGS. 7 and 8, the vacuum container 102 is constructed as a female member having a cylindrical recess 107 therein adapted to receive an adapter 103 which is constructed in the form of a male member adapted to mate with the cylindrical recess 107. Thus, as can be seen in the arrangement shown in FIG. 1, the first and second needles 53 and 54 are coaxially disposed with respect to each other whereas in the embodiment shown in FIG. 7, the first and second needles 126 and 131 are disposed side by side.

In operation of the apparatus shown in FIGS. 7 and 8, when the aspiration needle has been positioned so that the distal extremity 18 of the aspiration needle 12 is disposed within the tumor, the vacuum container 102 can be pressed forwardly or proximally against the force of the conical coil spring 136 to a first position to cause the proximal extremity 127 of the first needle to penetrate the diaphragm 112 and to expose the aspiration needle 12 to the subambient pressure provided in the vacuum container 102 to cause aspirate to be drawn into the chamber of the aspiration needle 12 in the manner hereinbefore described. When a sufficient sample has been collected, the vacuum container 102 can be further depressed to cause the proximal extremity 132 of the second needle 132 to puncture the diaphragm to expose the evacuated space 111 in the vacuum container 12 to ambient through the port 121 to break the subambient condition being applied to the aspiration needle 12 to thereby terminate collection of aspirate. Thereafter, the needle aspiration apparatus 101 can be removed and the sample collected in the aspiration needle treated in the manner hereinbefore described.

It is apparent from the foregoing that there has been provided an aspiration needle apparatus 11 which facilitates collection of aspirate and cell samples as for example in tumors and the like. This collection is enhanced because it eliminates the necessity for the physician or surgeon doing the procedure to utilize a syringe or other vacuum source to create the necessary subambient condition in the aspiration needle. By utilizing a pre-packaged vacuum container to supply the desired subambient condition to the needle for an appropriate period of time, the collection of the appropriate cell sample is greatly enhanced. Thus it is possible to readily collect cell samples without the necessity of having a syringe or other accessory devices as for example a vacuum pump to supply the subambient condition. Also by providing a vacuum container having a predetermined volume of evacuated space, it is possible to program the subambient pressure applied to the aspiration needle 12 to also predetermine the maximum amount of time that a subambient pressure will be applied to the aspiration needle. In addition, the aspiration needle apparatus of the present invention is relatively simple. It can be readily manufactured. If desired, it can be supplied in kit form.

Figures 9, 10, 11, 12, 13:
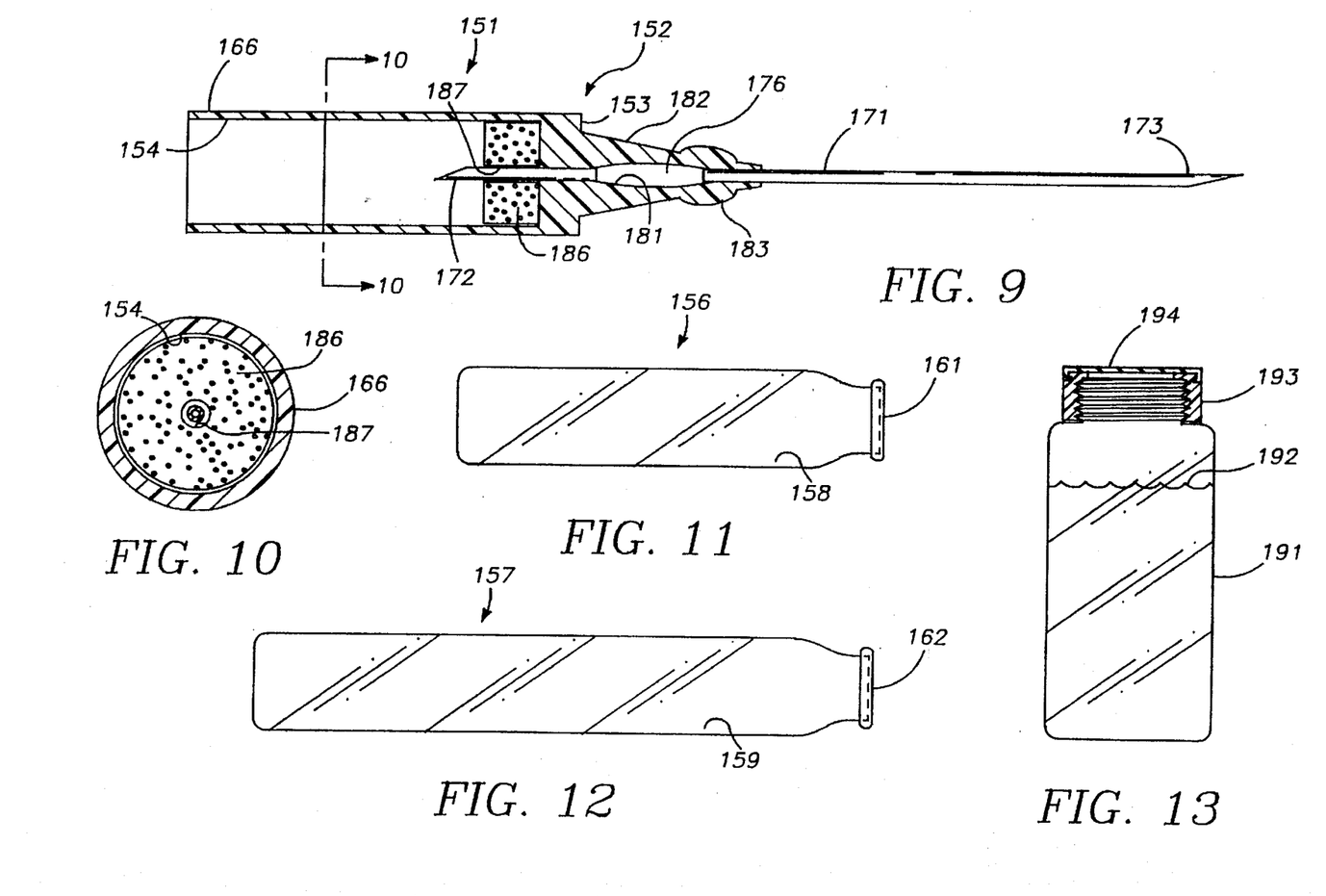
FIG. 9 is a side elevational view in section of another embodiment of an aspiration needle apparatus incorporating the present invention.
FIG. 10 is a cross sectional view taken along the line 10-1 of FIG. 9.
FIG. 11 is a side elevational view of a small vacuum container utilized with the apparatus shown in FIG. 9.
FIG. 12 is a side elevational view of a large vacuum container used with the apparatus shown in FIG. 9.
FIG. 13 is a side elevational view of a bottle containing a medium for use with the apparatus shown in FIG. 9.

Still another embodiment of the aspiration needle apparatus incorporating the present invention is shown in FIGS. 9 and 10. The aspiration needle apparatus 151 consists of an adapter 152 which can be formed of a suitable material such as plastic. The adapter 152 consists of a body 153 which is provided with a cylindrical bore 154 sized to receive either a small vacuum container 156 shown in FIG. 11 or a large vacuum container 157 shown in FIG. 12. Both of the vacuum containers 156 and 157 are cylindrical as shown and have basically the same diameter with the large vacuum container 157 having a greater length than the small vacuum container 156. The evacuated space 158 in the small vacuum container 156 can be of a suitable size as for example 20-30 milliliters, whereas the evacuated space 159 in the large vacuum container 157 can be of a suitable size as for example 30-60 milliliters. These evacuated spaces are accessible by a needle which can penetrate penetrable diaphragms 161 and 162, respectively which seal the containers. As shown in FIG. 9, the bore 154 in the body 153 forms a cylindrical sleeve 166 into which the vacuum containers 156 and 157 can be inserted.

Needle means 171 is carried by the body 153 of the adapter 152 and has a proximal extremity 172 which extends into the bore 154 that serves as a penetrating needle and a distal extremity 173 extending distally of the body 153 which serves as an aspiration needle. A cell collection chamber 76 is provided as a part of the needle means and is disposed between the proximal and distal extremities 172 and 173 of the needle means. It is possible that the needle means 171 be formed as a single needle of a suitable material such as stainless steel. However, in accordance with the present invention it is preferable to form the needle means with the distal extremity 173 being a separate aspiration needle of the type hereinbefore described and the proximal extremity 172 being formed as a separate penetrating needle also of the type hereinbefore described. When formed as separate needles, the needles can be embedded within the body 153 and having the flow passage therein in communication with a flow passage 181 in communication with the cell collection chamber 176 which also can be formed in the tapered conical extension 182. As previously disclosed, the conical extension 182 can be provided with a convex portion 183 which surrounds the cell collection chamber 176 to provide magnification means for viewing the cell sample collected within the cell collection chamber 176. Thus the flow passage in the distal extremity 173, the cell collection chamber 176 and the flow passage 181 are in communication with the flow passage in the proximal extremity 172 and in communication with the interior of the sleeve 166. Yieldable means in the form of a foam rubber disc 186 is provided within the bore 154 and has a bore 187 therein through which the proximal extremity 172 of the needle means 171 extends. It is generally preferable that the proximalmost extremity of the proximal extremity 172 of the needle means 171 protrude slightly above the proximal surface of the yieldable means 186.

The apparatus shown in FIG. 9 can be used with a medium bottle or container 191 such as shown in FIG. 13 in which the medium is carried within the bottle and is accessible through a cap 193 threaded onto the bottle and having a penetrable diaphragm 194 carried thereby giving access to the medium 192.

Figures 14, 15:
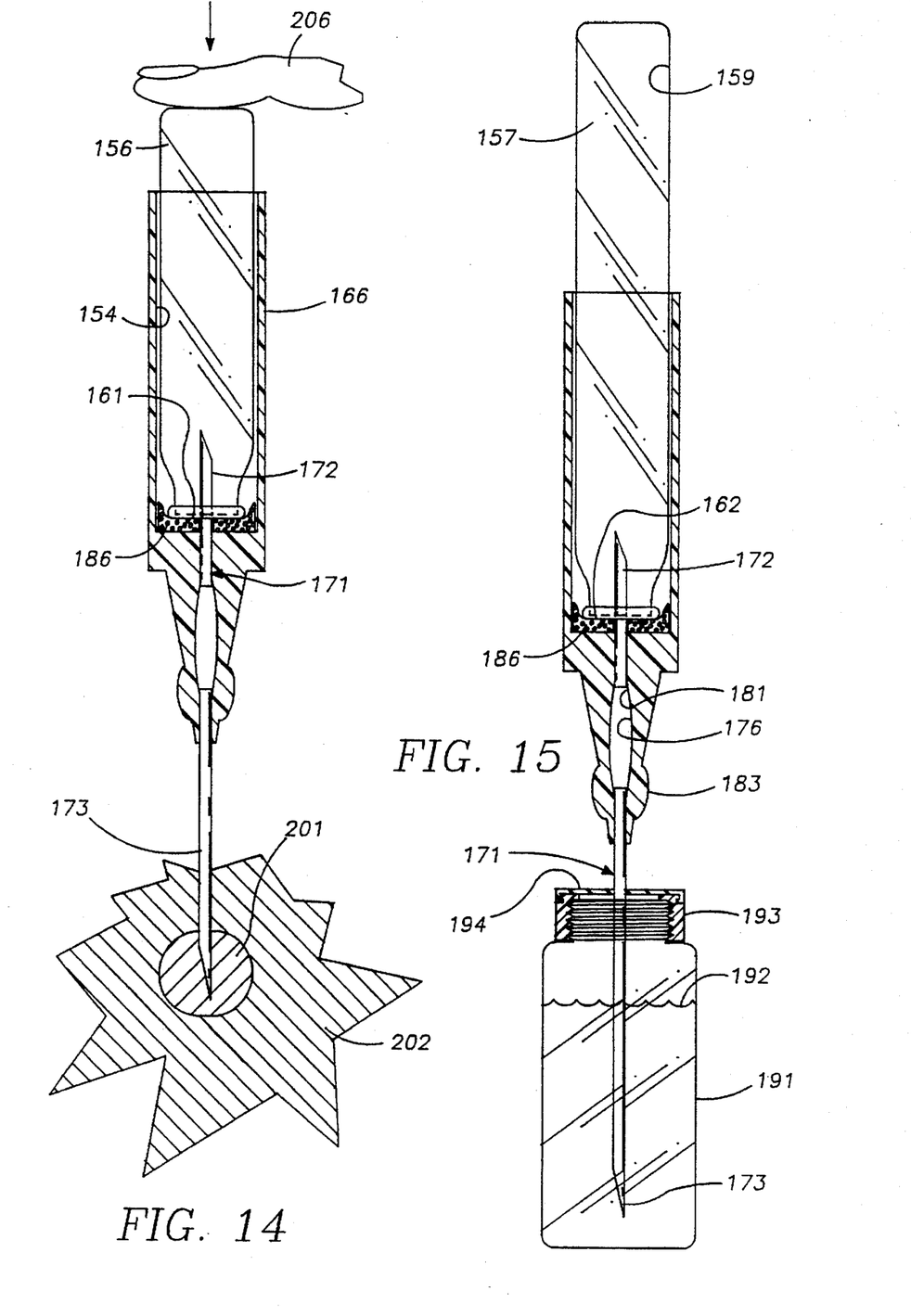
FIG. 14 is an illustration showing the manner in which the aspiration needle apparatus shown in FIGS. 9 through 11 can be utilized for collecting a cell sample in tissue as for example from a tumor in the tissue.
FIG. 15 is an illustration showing the manner in which the cell sample collected in the needle apparatus shown in FIG. 14 is sucked out of the needle along with a medium and into the large vacuum container shown in FIG. 12 with the medium being taken from the container shown in FIG. 13.

Operation and use of the aspiration needle apparatus shown in FIGS. 9 through 13 may now be briefly described as follows. The physician picks up the adapter 152 and places the small vacuum container 156 within the bore 154 of the sleeve 166 with yieldable means 186 serving to prevent the proximal extremity 172 of the needle means 171 from penetrating the diaphragm 161. The physician, while holding the adapter 152 in one hand utilizes the other hand to localize the lump which is to be analyzed and keeps it in position while the other hand is utilized to cause the distal extremity 173 of the needle means 171 to penetrate the lump within the tissue. If desired, ultrasound can be utilized for aiding and locating the lump to be analyzed. As shown in FIG. 15, the distal extremity 173 has been positioned within a lump 201 in tissue 202.

As soon as the distal extremity 173 of the needle means 171 has been properly positioned within the lump 201, the forefinger 206 of the hand holding the adapter 152 can be used to urge the small vacuum container 156 inwardly against the force of the yieldable means 186 to cause the proximal extremity 172 to penetrate the diaphragm 161 to establish communication with the evacuated space 158 and the flow passage in the needle means so that a vacuum is supplied to the distal extremity 173 disposed within the lump or tumor 201. The needle means 171 is kept steady by the physician's index finger and thumb while maintaining the vacuum condition and the needle means 171 by the forefinger continuously applying pressure to the small vacuum container 156. By holding the adapter 152 in this manner, it is possible for the physician to gently pass the distal extremity 173 back and forth through the tumor to ensure that an adequate cell sample has been collected which can be ascertained by viewing the collection of the cell sample in the collection chamber 166 through the magnifying bulb 183.

As soon as an adequate cell sample has been collected, the vacuum being applied to the needle means 171 is terminated by the forefinger releasing the small container 156 permitting the yieldable means 186 to urge the small vacuum container 156 axially away from the proximal extremity 172 of the needle means 171. The distal extremity 173 of the needle means 171 is then removed from the tissue 202 of the patient. The small vacuum container 156 is removed from the bore 154 and the large vacuum container 157 is placed in the bore 154 of the sleeve 166. The distal extremity 173 of the needle means 171 is then covered to penetrate the diaphragm 194 of the medium container 191. As soon as the distal extremity is submersed within the medium 192, the large vacuum container 157 can be pressed by the forefinger of the hand to cause the proximal extremity 172 to penetrate the diaphragm 172 to couple the evacuated space to the flow passage in the needle means 171 to suck up medium 192 to the flow passage into the needle means and to carry with it the cell sample collected within the collection chamber 176 and to bring the collected cells along with the medium into the interior of the vacuum container 157. As soon as the cell sample has been collected from the cell collection chamber, the large vacuum container 157 can be released by the forefinger permitting the yieldable means 186 to urge the large vacuum container off of the proximal extremity 172 of the needle means to interrupt supplying of a vacuum to the needle means 171.

The large vacuum bottle 157 containing the cell specimen along with medium can then be removed from the sleeve 166 and then shipped to a laboratory where the collected cells cab be evaluated.

It can be seen from the foregoing that there has been provided an aspiration needle apparatus that is very simple in construction and can be readily used for collecting cell samples. The cell sample collected in the collection chamber of the needle means can be readily removed from the needle means by use of a second vacuum container and sucking the cell collection from the collection chamber by sweeping the cell collection out by the use of a medium also aspirated into a large vacuum container for later shipment to a laboratory for analysis. This eliminates the need to supply a needle with the cell collection therein to a laboratory. It also eliminates the need for a double lumen needle of the type hereinbefore described.

It should be appreciated that it is possible if there is a large enough vacuum container available to utilize a single vacuum container for performing the aspiration and collection functions hereinbefore described by the small and large vacuum containers. However, it may be undesirable to use a single vacuum container because there is a possibility of air being introduced into the vacuum container as the cells are being collected from tissue of the patient. It can be seen that a flow passage construction has been provided for the collection of the cells so that cells will not become entrapped in the needle means. Also it can be seen that the needle aspiration apparatus of the present invention is very simple and inexpensive and greatly facilitates the collection of cell samples free of contamination.

We claim:

1. An aspiration needle apparatus for collecting cell samples from tissue for use by a human operator having a hand with fingers thereon comprising a vacuum container having an enclosed evacuated space evacuated to a subambient pressure which provides a predetermined volume of evacuated space devoid of a solid or a liquid and devoted solely to providing the desired vacuum and sealed by a penetrable diaphragm, an adapter having a recess receiving said vacuum container and needle means carried by the adapter and having a distal extremity serving as an aspiration needle to collect the cell sample and having a proximal extremity disposed in said recess and being capable of penetrating the diaphragm to couple the evacuated space to the flow passage of the needle means to supply a subambient pressure to the distal extremity of the needle means and yieldable means disposed within the recess and engaged by the vacuum container for yieldably retaining the vacuum container out of engagement with the proximal extremity of the needle means and applying a force which can be readily overcome by a finger of the hand so that the proximal extremity of the needle means can be caused to penetrate the diaphragm.

2. Apparatus as in claim 1 wherein said needle means includes a collection chamber disposed between the proximal and distal extremities of the needle means.

3. Apparatus as in claim 2 further including magnification means carried by the needle means for magnifying the interior of the collection chamber.

4. An aspiration needle apparatus for collecting cell samples from tissue of a patient comprising a vacuum container having an enclosed evacuated space evacuated to a subambient pressure which provides a predetermined volume of evacuated space devoid of a solid or a liquid and devoted solely to providing the desired vacuum accessible through a penetrable diaphragm, an aspiration needle having proximal and distal extremities and having a flow passage extending from the proximal extremity to the distal extremity, an adapter carried by the proximal extremity of the aspiration needle, means carried by the adapter for providing a cell collection chamber proximal of the proximal extremity of the aspiration needle, a penetrating needle mounted in the adapter and having proximal and distal extremities and having a flow passage extending from the proximal extremity to the distal extremity in communication with the cell collection chamber, said adapter having a recess formed therein in communication with the flow passage and the proximal extremity of the penetrating needle so that when said vacuum container is placed in said recess with said diaphragm facing into the recess the vacuum container can be moved to cause the penetrating needle to penetrate the diaphragm to couple the evacuated space in the vacuum container to the flow passage in the penetrating needle to the cell collection chamber and to the aspiration needle.

5. Apparatus as in claim 4 for use by an operator having a hand with fingers thereon, further including yieldable means carried by the adapter and disposed within the recess for urging the vacuum container in a direction away from the proximal extremity of the penetrating needle and applying a force which can be readily overcome with a finger of the hand.

6. An aspiration needle aparatus for collecting cell samples comprising an aspiration needle having proximal and distal extremities and having a flow passage extending from the proximal extremity to the distal extremity, the proximal extremity having a hub formed thereon, a vacuum container having an enclosed evacuated space evacuated to a subambient pressure which provides a predetermined volume of evacuated space devoid of a solid or a liquid and devoted solely to providing the desired vacuum and carrying a penetrable diaphragm providing access to the evacuated space, an adapter removably mounted on the hub and making a fluid-tight connection therewith and having a flow passage therein in communication with the flow passage in the aspiration needle, said adapter being formed to receive said vacuum container and receiving said vacuum container, said adapter including first and second needle means carried thereby having flow passages therein and having proximal extremities which are offset in an axial direction with respect to each other with the first needle means having a flow passage therein in communication with the flow passage in the aspiration needle and with the second needle means being disposed distally from the first needle means and in communication with the flow passage in the body of the adapter and open to atmospheric pressure, said adapter and said vacuum container being formed so as to permit relative movement between the adapter and the vacuum container to first permit the first needle means to puncture the diaphragm of the vacuum container to connect the evacuated space having ambient pressure in the vacuum container to the aspiration needle to supply the subambient pressure to the aspiration needle and upon further relative movement permitting the second needle means to puncture the diaphragm to expose the evacuated space to atmospheric pressure to interrupt the application of subambient pressure to the aspiration needle.

7. Apparatus as in claim 6 wherein said aspiration needle is provided with a collection chamber therein.

8. Apparatus as in claim 6 wherein said second needle means is coaxially mounted on the first needle.

9. Apparatus as in claim 6 wherein said first and second needle means are mounted side by side.

10. Apparatus as in claim 6 for use by an operator having a hand with fingers thereon further including yieldable spring means disposed between the vacuum container and the adapter for yieldably retaining the diaphragm out of engagement with the first and second needles means to prevent inadvertent puncture of the diaphragm by the first and second needle means and applying a force which can be readily overcome by a finger of the hand.

11. Apparatus as in claim 6 wherein said vacuum container is formed as a male member and wherein said adapter is formed as a female member permitting said vacuum container to cooperatively mate with the adapter.

12. Apparatus as in claim 6 wherein said vacuum container is formed as a female member having a cylindrical recess therein and wherein said adapter is formed as a male member adapted to enter the cylindrical recess of the female member and to slidably mate therewith.

13. Apparatus as in claim 6 wherein said first and second needle means includes a mounting block disposed in the flow passage of the adapter, a first needle being mounted in the mounting block and extending through the mounting block, a second needle being coaxially mounted on the first needle and spaced proximally of the mounting block and a flow passage in the adapter being on the side of the mounting block opposite the distal extremity and being open to the atmosphere.

14. An adapter for use with an aspiration needle and a vacuum container for supplying a subambient condition to the aspiration needle from the vacuum container, the vacuum container having an evacuated space therein evacuated to a subambient pressure which provides a predetermined volume of evacuated space devoid of a solid or a liquid and devoted solely to providing the desired vacuum and a puncturable diaphragm providing access to the evacuated space, the adapter comprising e body having proximal and distal extremities and having a flow passage extending from the proximal extremity to the distal extremity, the distal extremity being formed to mate with the aspiration needle to form a fluid-tight seal therewith and first and second needles carried by the body of the adapter and each having a flow passage therein, the first needle having a proximal extremity offset proximally from the proximal extremity of the second needle, said body having a flow passage therein in communication with the flow passage in the first needle and extending through the distal extremity of the body, said second needle being in communication with the flow passage in the body, said body being formed to provide a space to receive the vacuum container and to permit the first needle to penetrate the puncturable diaphragm wherein the first needle is used to supply the subambient condition to the aspiration needle and to thereafter permit the second needle to penetrate the puncturable diaphragm whereby the subambient condition to the aspiration needle is terminated.

15. An adapter as in claim 14 wherein said first and second needles are coaxially disposed with respect to each other.

16. An adapter as in claim 14 wherein said first and second needles are mounted side by side.

17. An adapter as in claim 14 wherein said body has an opening therein open to ambient and wherein said flow passage in the second needle is exposed to ambient through said opening in the body.

18. A method for withdrawing aspirate in the form of cells from tissue in a body by the use of an aspiration needle and a vacuum container having an evacuated space therein evacuated to a subambient pressure accessible through a puncturable diaphragm, the aspiration needle having a collection chamber and a tubular member having a sharpened distal extremity and having a flow passage therein extending into the collection chamber and extending through the sharpened distal extremity comprising puncturing the diaphragm of the vacuum container to couple the evacuated space in the vacuum container to the collection chamber and to supply a subambient pressure from the evacuated space in the vacuum container to the tubular member to cause aspirate from the tissue to be drawn as a cell sample into the collection chamber and exposing the evacuated space in the vacuum container to atmosphere when sufficient aspirate has been collected in the collection chamber from the tissue to terminate the supplying of subambient pressure to the tubular member to thereby terminate the collection of aspirate from the tissue.

19. A method as in claim 18 for use with a medium container introducing the aspiration needle into the medium container and moving the vacuum container to cause the evacuated space therein to be placed in communication with the aspiration needle to cause medium to be sucked from the medium container into the aspiration needle and to carry with it the cell sample which has been collected into the evacuated space and separating the vacuum container from the aspiration needle.

20. A method as in claim 18 wherein a second vacuum container is utilized and wherein the step of collecting the cell sample and the medium is accomplished by utilizing the second vacuum container.

\* \* \* \* \*